(12) United States Patent
Down et al.

(10) Patent No.: US 9,717,451 B2
(45) Date of Patent: Aug. 1, 2017

(54) DEVICE FOR WITHDRAWING OR ADMINISTERING A SUBSTANCE AND METHOD OF MANUFACTURING A DEVICE

(75) Inventors: James Down, Cary, NC (US); Noel G. Harvey, Efland, NC (US); Frank E. Martin, Durham, NC (US); Ronald J. Pettis, Durham, NC (US); Alexander G. Lastovich, Raleigh, NC (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 1070 days.

(21) Appl. No.: 13/442,933

(22) Filed: Apr. 10, 2012

(65) Prior Publication Data

US 2013/0263997 A1    Oct. 10, 2013
US 2016/0207253 A9    Jul. 21, 2016

Related U.S. Application Data

(62) Division of application No. 10/443,822, filed on May 23, 2003, now Pat. No. 8,172,815, which is a division of application No. 09/590,062, filed on Jun. 8, 2000, now Pat. No. 6,607,513.

(51) Int. Cl.
| | |
|---|---|
| *B32B 37/00* | (2006.01) |
| *A61B 5/15* | (2006.01) |
| *A61M 37/00* | (2006.01) |
| *A61M 5/32* | (2006.01) |
| *B29C 65/08* | (2006.01) |
| *B29L 31/00* | (2006.01) |

(52) U.S. Cl.
CPC ..... *A61B 5/150282* (2013.01); *A61M 5/3298* (2013.01); *A61M 37/0015* (2013.01); *B29C 65/08* (2013.01); *A61M 2037/0046* (2013.01); *A61M 2037/0053* (2013.01); *A61M 2207/00* (2013.01); *B29L 2031/7544* (2013.01); *Y10T 29/49826* (2015.01); *Y10T 156/10* (2015.01)

(58) Field of Classification Search
CPC .......................... A61M 37/0015; B29C 65/08
USPC ........ 156/73.1, 293, 297, 298, 308.2, 580.1, 156/580.2
See application file for complete search history.

(56) References Cited

U.S. PATENT DOCUMENTS

| | | | |
|---|---|---|---|
| 3,964,482 A | 6/1976 | Gerstel et al. | |
| 4,695,273 A * | 9/1987 | Brown | .......................... 604/173 |
| 5,250,023 A | 10/1993 | Lee et al. | |
| 5,287,852 A | 2/1994 | Arkinstall | |

(Continued)

FOREIGN PATENT DOCUMENTS

| | | |
|---|---|---|
| EP | 0205915 A1 | 12/1986 |
| WO | 9748440 A1 | 12/1997 |
| WO | 9964580 A1 | 12/1999 |

*Primary Examiner* — James Sells
(74) *Attorney, Agent, or Firm* — The Webb Law Firm

(57) ABSTRACT

A device includes a plurality of skin penetrating devices for delivering or withdrawing a substance through the skin of a patient. The device has a support formed with a top and bottom end and a plurality of channels extending axially through the support. A plurality of the skin penetrating members is positioned in the channels with a tip extending from the bottom end of the support. A coupling member is attached to the support for coupling with a fluid supply and directing the fluid to the skin penetrating members. The skin penetrating members have a length of about 100 microns to about 2000 microns and are about 30 to 50 gauge.

10 Claims, 10 Drawing Sheets

(56) References Cited

U.S. PATENT DOCUMENTS

| | | |
|---|---|---|
| 5,288,290 A | 2/1994 | Brody |
| 5,306,259 A | 4/1994 | Fischell et al. |
| 5,879,326 A | 3/1999 | Godshall et al. |
| 6,183,489 B1 * | 2/2001 | Douglas ............... A61B 5/1411 |
| | | 600/583 |
| 6,190,367 B1 | 2/2001 | Hall |
| 6,312,612 B1 * | 11/2001 | Sherman ................... B26F 1/24 |
| | | 216/11 |
| 6,322,808 B1 | 11/2001 | Trautman et al. |
| 6,379,324 B1 | 4/2002 | Gartstein et al. |
| 6,440,096 B1 * | 8/2002 | Lastovich et al. .............. 604/27 |
| 6,451,240 B1 | 9/2002 | Sherman et al. |
| 6,485,461 B1 | 11/2002 | Mason et al. |
| 6,497,868 B1 | 12/2002 | Tanahashi |
| 6,537,242 B1 * | 3/2003 | Palmer ............................ 604/22 |
| 6,607,513 B1 * | 8/2003 | Down et al. ................... 604/239 |
| 6,638,258 B2 | 10/2003 | Schwartz et al. |
| 6,695,822 B2 | 2/2004 | Adams et al. |
| 7,186,235 B2 | 3/2007 | Martin et al. |
| 7,896,837 B2 | 3/2011 | Wilkinson et al. |
| 7,914,480 B2 | 3/2011 | Cleary et al. |
| 2003/0187423 A1 * | 10/2003 | Wilkinson et al. ........... 604/506 |

* cited by examiner

DEVICE FOR WITHDRAWING OR ADMINISTERING A SUBSTANCE AND METHOD OF MANUFACTURING A DEVICE

CROSS REFERENCE TO RELATED APPLICATIONS

This application is a divisional of U.S. patent application Ser. No. 10/443,822, now U.S. Pat. No. 8,172,815, filed May 23, 2003, which was a divisional of U.S. patent application Ser. No. 09/590,062, now U.S. Pat. No. 6,607,513, filed Jun. 8, 2000.

FIELD OF THE INVENTION

The present invention relates to a device for administering a substance, such as a drug or pharmaceutical agent, or withdrawing a substance transdermally to a patient. More particularly, the invention is directed to a device having an array of penetrating members and a method of manufacturing an array for delivering or removing a substance from a patient.

BACKGROUND OF THE INVENTION

Various substances are extracted from or delivered to the body by many known processes. One method that is often used is the subcutaneous delivery using a needle or other cannula. The use of a needle cannula is an effective method of extracting or delivering a substance but is often painful to the patient. The pain typically experienced by the patient has prompted the development of alternative methods for extracting or delivering drugs.

Various devices have been proposed for introducing substances to the body by transdermal delivery methods. Transdermal delivery devices are often used to provide a sustained release of the drug to maintain a desired rate of delivery. Many transdermal delivery devices are not able to administer drugs at a sufficient rate to be used effectively. Moreover, many drugs can not be delivered transdermally since the drugs are not able to pass through the protective skin layers.

The skin is made up of several layers with the upper composite layer being the epithelial layer. The outermost layer of the skin is the stratum corneum that has well known barrier properties to prevent molecules and various substances from entering the body and analytes from exiting the body. The natural impermeability of the stratum corneum prevents the administration of most pharmaceutical agents and other substances through the skin. The stratum corneum is a complex structure of compacted keratinized cell remnants having a thickness of about 10-30 microns. The stratum corneum forms a waterproof membrane to protect the body from invasion by various substances and the outward migration of various compounds.

Numerous methods and devices have been proposed to enhance the permeability of the skin and to increase the diffusion of various substances through the skin to be utilized by the body. Typically, the delivery of drugs through the skin is enhanced by either increasing the permeability of the skin or increasing the force or energy used to direct the drug through the skin.

One example of a method for increasing the delivery of drugs through the skin is iontophoresis. Iontophoresis generally applies an external electrical field to ionize the drug, thereby increasing the diffusion of the drug through the skin. Iontophoresis can be difficult to control the amount and rate of drug delivery. Under some circumstances, iontophoresis can cause skin damage depending on the extent of ionization, the energy applied to ionize the drug and duration of the treatment.

In recent years there has been an increased interest in micro devices for delivering drugs through the skin is by forming micropores or cuts through the stratum corneum. By penetrating the stratum corneum and delivering the drug to the skin in or below the stratum corneum, many drugs can be effectively administered. The devices for penetrating the stratum corneum generally include a plurality of micron size needles or blades having a length to penetrate the stratum corneum without passing completely through the epidermis. Examples of these devices are disclosed in U.S. Pat. No. 5,879,326 to Godshall et al.; U.S. Pat. No. 5,250,023 to Lee et al., and WO 97/48440.

The micro devices that are commonly used are often manufactured using various techniques such as stereo lithography. These techniques can be used effectively to manufacture devices of a few microns and are able to form channels and other shapes for the delivery of fluids. A disadvantage of the devices is the cost of the manufacturing process and the time required to produce a single item. Other processes such as wet etching, plasma etching and machining can produce fine details in the finished substrate but are not cost or time effective for commercial use.

The prior manufacturing methods and devices for the transdermal administration of drugs have exhibited limited success. Accordingly, a continuing need exists in the industry for an improved device for the administration of various drugs and other substances.

SUMMARY OF THE INVENTION

The present invention is directed to a device for withdrawing or delivering a substance to a patient. In particular, the invention is directed to a method and apparatus for penetrating the skin to a sufficient depth where an analyte or other substance can be withdrawn or a pharmaceutical agent can be absorbed and utilized by the body. The invention is further directed to a method of manufacturing the device for withdrawing or delivering a substance to a patient.

Accordingly, a primary object of the invention is to provide a device for efficiently sampling or administering a substance transdermally through the skin substantially without pain to the patient.

Another object of the invention is to provide a device having a plurality of cannulas for penetrating the outer layers of the skin for withdrawing a sample or delivering a substance to the skin.

A further object of the invention is to provide a device for withdrawing a sample or delivering a substance. The device has a plurality of penetrating members in a support where the penetrating members have a distal end extending from the support a distance of about 50 microns to about 2 mm.

Another object of the invention is to provide a sampling or delivery device having a plurality of needles formed into an array in a substrate for penetrating the outer layers of the skin of a patient.

Still another object of the invention is to provide a sampling or delivery device having an array of needles extending from a support a distance of at least 100 microns for penetrating the skin.

Another object of the invention is to provide a device for sampling or delivering a substance having a plurality of cannulas with a length of about 100 to about 500 microns.

A further object of the invention is to provide a device for sampling or delivering a substance having a plurality of cannulas with a length of greater than 500 microns.

Another object of the invention is to provide a device for sampling or delivering a substance having a plurality of stainless steel cannulas.

These and other objects of the invention are substantially attained by providing a device for the intradermal withdrawing or delivery of a substance to a patient. The device comprises a support having a top end and a bottom end. The support has at least one channel extending from the top end to the bottom end. A skin penetrating member is positioned in the channel and is coupled to the support. The skin penetrating member has an exposed end extending from the bottom end of the support a distance sufficient to penetrate the skin of a patient.

The objects and advantages of the invention are further attained by providing a device for the intradermal withdrawing or delivery of a substance to a patient. The device comprises a support having an axial dimension with a top end and a bottom end and a plurality of spaced-apart axial channels extending from the top end to the bottom end. A skin penetrating member is positioned in each of the channels. Each of the skin penetrating members has a first end coupled to the housing and a second end extending axially from the bottom end of the support.

The objects of the invention are further attained by providing a method of manufacturing a skin penetrating device by the steps of providing a support having an axial dimension with a top end and a bottom end and a plurality of spaced apart channels extending from said bottom end in said axial dimension, and positioning a skin penetrating member in each of the axial channels, where the skin penetrating member has a first end coupled to the housing and a second end spaced from the bottom end.

The objects of the invention are still further attained by providing a method of forming a skin penetrating device comprising the steps of: providing a support having an axial dimension with a top end and a bottom end and at least one axial channel extending from the bottom end; and positioning a skin penetrating member completely in the axial channel and coupling the skin penetrating member to the support; and removing a portion of the bottom end of the support and exposing an end of the skin penetrating member.

The objects, advantages and other salient features of the invention will become apparent from the following detailed description which, taken in conjunction with the annexed drawings, discloses preferred embodiments of the invention.

BRIEF DESCRIPTION OF THE DRAWINGS

The following is a brief description of the drawings in which.

DETAILED DESCRIPTION OF THE PREFERRED EMBODIMENTS

Figure 1:
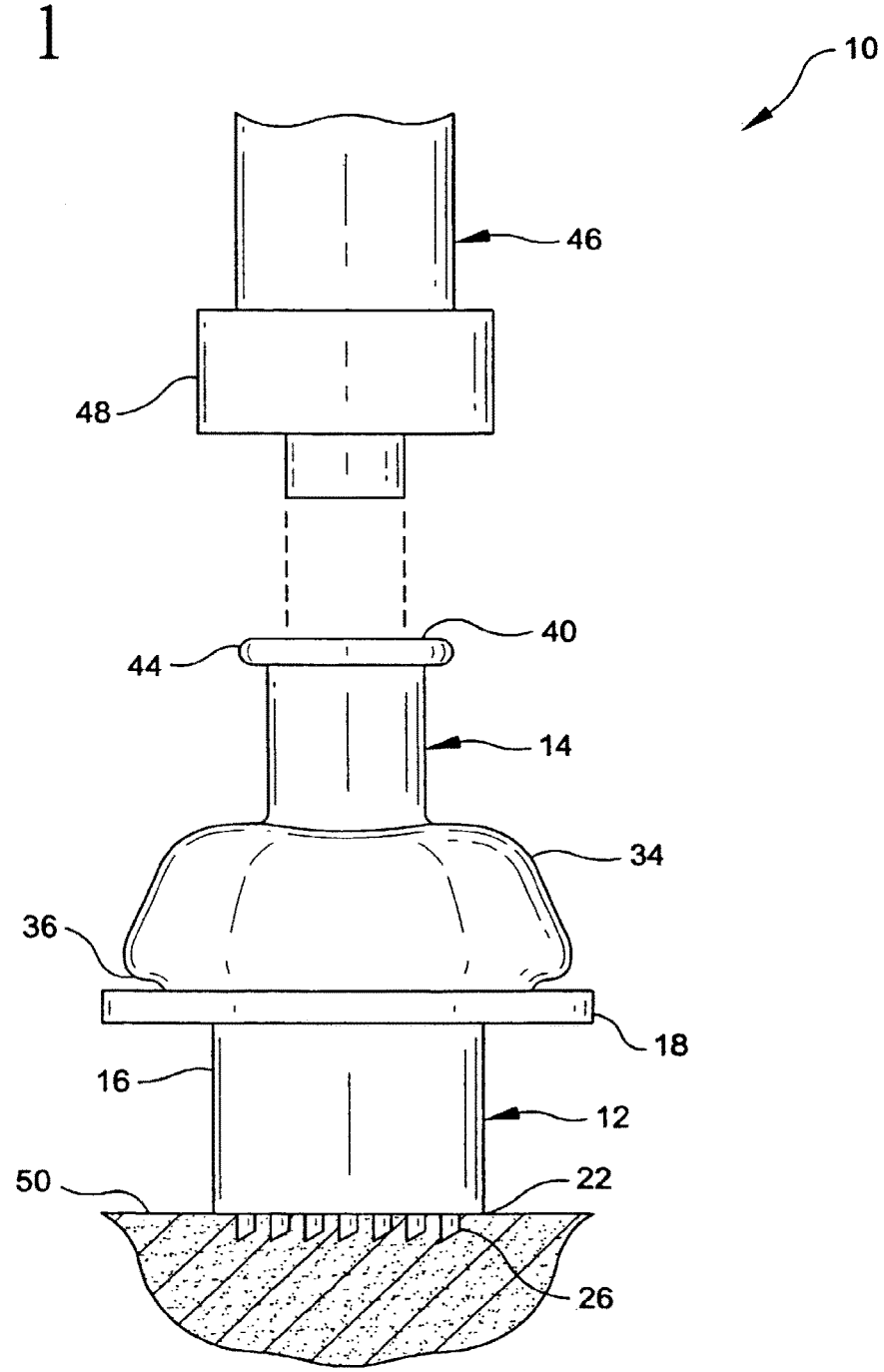
FIG. 1 is a side elevational view of a transdermal delivery device in accordance with a first embodiment of the invention.

The present invention is directed to a device for withdrawing a sample or administering a substance to a patient. More particularly, the invention is directed to a sampling or delivery device and to a method for withdrawing a substance or administering a substance into or below the stratum corneum of the skin of a patient. The invention is also directed to a method of forming a skin penetrating device and a sampling or delivery device. As used herein, the term penetrate refers to entering a layer of the skin without passing completely through. Piercing refers to passing completely through a layer of the skin. The term skin penetrating device refers to a device that is able to pierce or penetrate the skin to a desired depth.

The device and method of the present invention are particularly suitable for use in administering various substances, including pharmaceutical agents, to a patient, and particularly to a human patient. The device of the invention is also suitable for withdrawing substances from the body of a patient. Examples of substances that can be withdrawn from the body include glucose, electrolytes, alcohol, drugs and the like. As used herein, a pharmaceutical agent includes a substance having biological activity that can be delivered through the body membranes and surfaces, and particularly the skin. Examples include antibiotics, antiviral agents, analgesics, anesthetics, anorexics, antiarthritics, antidepressants, antihistamines, anti-inflammatory agents, antineoplastic agents, vaccines, including DNA vaccines, and the like. Other substances that can be delivered intradermally to a patient include proteins, peptides and fragments thereof. The proteins and peptides can be naturally occurring, synthesized or recombinantly produced.

The primary barrier properties of the skin including the resistance to drug penetration reside in the outermost layer or stratum corneum of the skin. Once a drug or other substance penetrates below the stratum corneum, there is substantially less resistance to permeation into the subsequent layers of the skin and eventual absorption by the body. Thus, delivery of a substance below the stratum corneum can be an effective system for administering some substances, and particularly some vaccines, to the body. The present invention is primarily directed to a device and method for delivering a substance, and particularly a pharmaceutical agent and vaccines, into or below the stratum corneum for administering the substance or pharmaceutical agent to the patient. In one embodiment, the device and method of the invention pierce the stratum corneum substantially without penetrating the dermis to target the tissue layers below the stratum corneum.

The sampling or delivery device is generally made from a plastic material that is non-reactive with the substance being administered. Suitable plastic materials include, for example, polyethylene, polypropylene, polyesters, polyamides and polycarbonates as known in the art. The cannulas can be made from various materials as known in the art. For example, microneedles can be made from silicon, stainless steel, tungsten steel, alloys of nickel, molybdenum, chromium, cobalt, and titanium, ceramics, glass, polymers and other non-reactive metals, and alloys thereof. In preferred embodiments of the invention the cannulas are stainless steel needles.

Referring to FIGS. 1-5, the device 10 in a first embodiment of the invention includes a support 12 for supporting at least one skin penetrating member 25. In this embodiment, device 10 is a sampling or delivery device and includes a coupling member 14.

Figure 2:
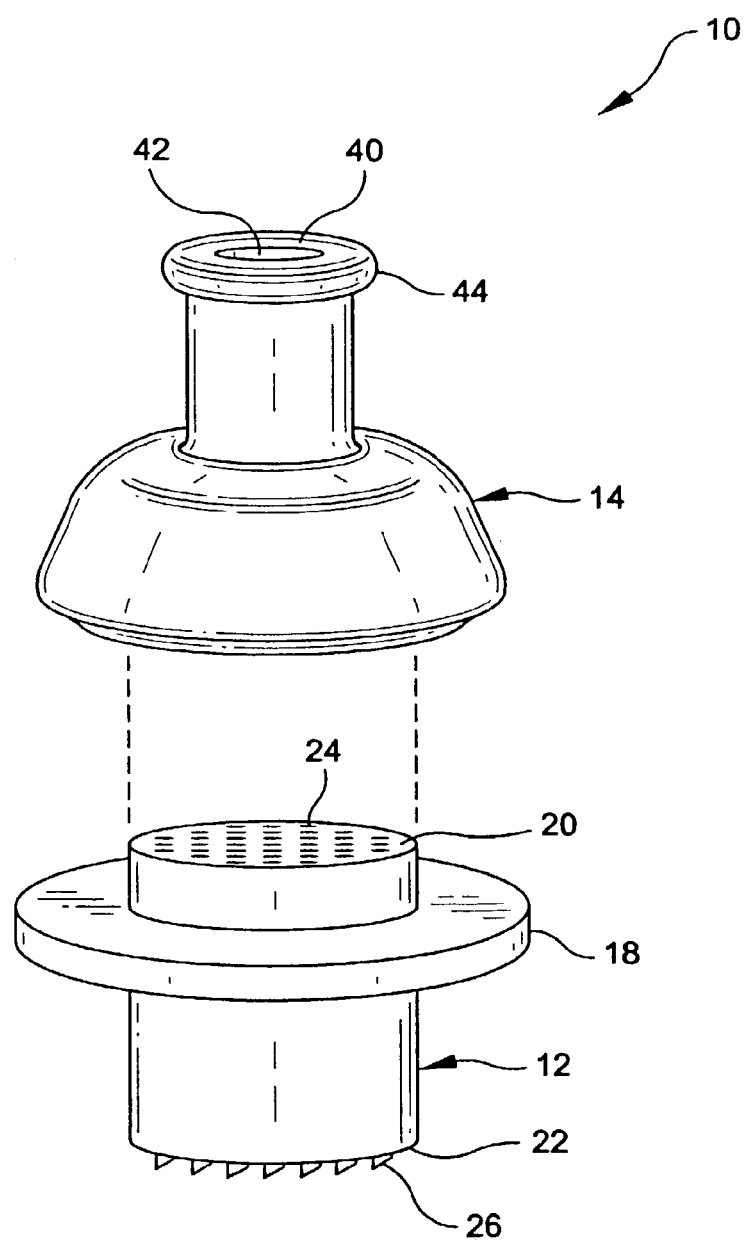
FIG. 2 is a perspective view of the transdermal delivery device of FIG. 1.

Support 12 in the embodiment illustrated has a substantially cylindrical body 16 adjacent a top end 20 of cylindrical body 16. As shown in FIG. 2, a flange 18 is spaced a small distance from top end 20 and extends outward from body 16. In alternative embodiments, flange 18 can be omitted. Top end 20 of cylindrical body 16 is substantially flat as shown in FIG. 2. Cylindrical body member 16 also includes a substantially flat bottom end 22 that is parallel to top end 20.

Figure 4:
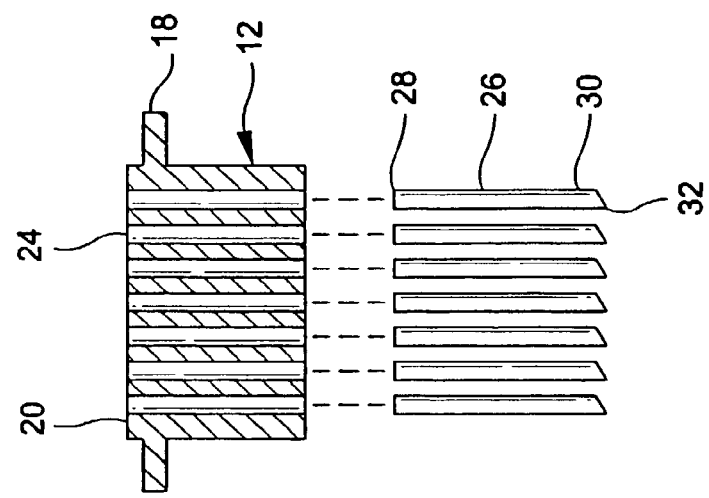
FIG. 4 is a side view in cross-section of the delivery device of FIG. 1 showing the support and cannulas.
Figure 3:
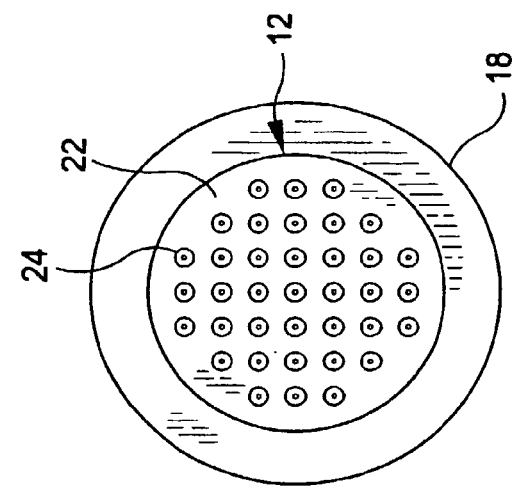
FIG. 3 is a bottom view of the transdermal delivery device of FIG. 1 showing the array of the cannulas.

As shown in FIGS. 3 and 4, cylindrical body 16 includes a plurality of channels 24 extending axially through the body 16 from top end 20 to bottom end 22. In the embodiment illustrated, a plurality of channels 24 are provided to form an array. Preferably, channels 24 are uniformly spaced apart a predetermined distance in a predetermined pattern. Skin penetrating member 25 in this embodiment is a plurality of cannulas 26 positioned in channels 24 and coupled to cylindrical body 16. It will be understood that the skin penetrating members are not limited to cannulas and that the cannulas are selected for illustrative purposes. In one preferred embodiment, cannulas 26 have a generally cylindrical shape with a top end 28 and a bottom end 30 terminating in a beveled tip 32. Preferably, cannulas 26 are positioned in channels 24 with the top end 28 of cannulas 26 substantially flush with top end 20 of cylindrical body 16. Cannulas 26 have a length sufficient to enable tip 32 of cannulas 26 to extend a predetermined distance from bottom end 22 of cylindrical body 16. In further embodiments, cannulas 26 can be positioned in channels 24 with top end 28 positioned above or below top end 20 of cylindrical body 16.

In the embodiment illustrated, support member 12 has a generally cylindrical shape. In further embodiments, can have other shapes depending on the particular needs and delivery site for the substance being delivered to the patient.

The length and thickness of the skin penetrating member 25 are selected based on the particular substance being administered and the desired depth of penetration of the skin penetrating members in the location where the delivery device is to be applied. In one embodiment, the cannulas pierce the stratum corneum and penetrate the epidermis. Alternatively, skin penetrating members can have a length to pass completely through the skin. The skin penetrating members can have an effective length ranging from about 100 to 2000 microns for penetrating the skin and generally at least about 100 microns. In one preferred embodiment, the skin penetrating members have an effective length of about 500 microns to about 1500 microns. In a further embodiment, the skin penetrating members have an effective length of about 700 microns to about 1250 microns. As used herein, the term "effective length" refers to the length of the skin penetrating members extending from bottom end 22 of body 12 and available for penetration into the skin of the patient.

The skin penetrating member in the illustrated embodiments are hollow cannulas having a generally cylindrical shape with a sharpened tip. In alternative embodiments, the skin penetrating members are microneedles having a conical, square or triangular shape, flat blades or pyramids. In still further embodiments, the skin penetrating member is a solid needle, microtube, blade or lancet. The microtubes can be glass tubes, glass capillaries or plastic tubes. Typically, the skin penetrating members are perpendicular to the plane of the device. In one embodiment, the skin penetrating members are hollow or solid needles of about 30 to about 50 gauge, and generally about 31 to 34 gauge to obtain optimum penetration of the skin. Generally, the array is formed from a plurality of identical skin penetrating members. In one embodiment, skin penetrating members having different widths can be used to form the array.

Cannulas in the embodiment illustrated have a sharpened tip formed by a single bevel. In further embodiments, the cannulas can be formed with multibevels, conical shaped tips or blunt tips. The bevels can be machined or formed on the cannulas before or after assembling into the support.

The arrangement and spacing of channels 24 define the pattern of the array of cannulas 26. In the embodiment of FIGS. 1-5, cannulas 26 are arranged in a generally circular pattern. In further embodiments, cannulas 26 can be arranged in a square, triangular or rectangular pattern depending on the delivery site and the substance being delivered. In still further embodiments, cannulas 26 can be arranged in an annular ring pattern.

Channels 24 can be formed using various techniques as known in the art. For example, channels can be formed by drilling, laser ablation, chemical etching or by directly molding the channels in the body as the body is manufactured. The channels are spaced to provide the desired density of the cannulas. The array of cannulas can have an area of about 1 to 5 cm$^2$ and can have a single cannula up to about 500 cannulas forming the array.

The method of forming the device by forming channels in a support provides a versatility that is not available with some microneedle manufacturing methods. By forming the channels in the support, the pattern of the array of penetrating members can be controlled as well as the size of the penetrating members forming the array.

Coupling member 14 includes a body portion 34 having a bottom end 36 with a central opening 38 and defining a cavity 39. Body portion 34 includes an open top end 40 and a hollow channel 42. Top end 40 includes a collar 44 for coupling with a fluid supply or fluid receiving reservoir. In the embodiment illustrated, collar 44 is a threaded collar dimensioned for coupling with a Luer fitting. In embodiments where top end 28 of cannulas 26 are positioned above top wall 20, cavity 39 accommodates the tops of cannulas 26.

Figure 5:
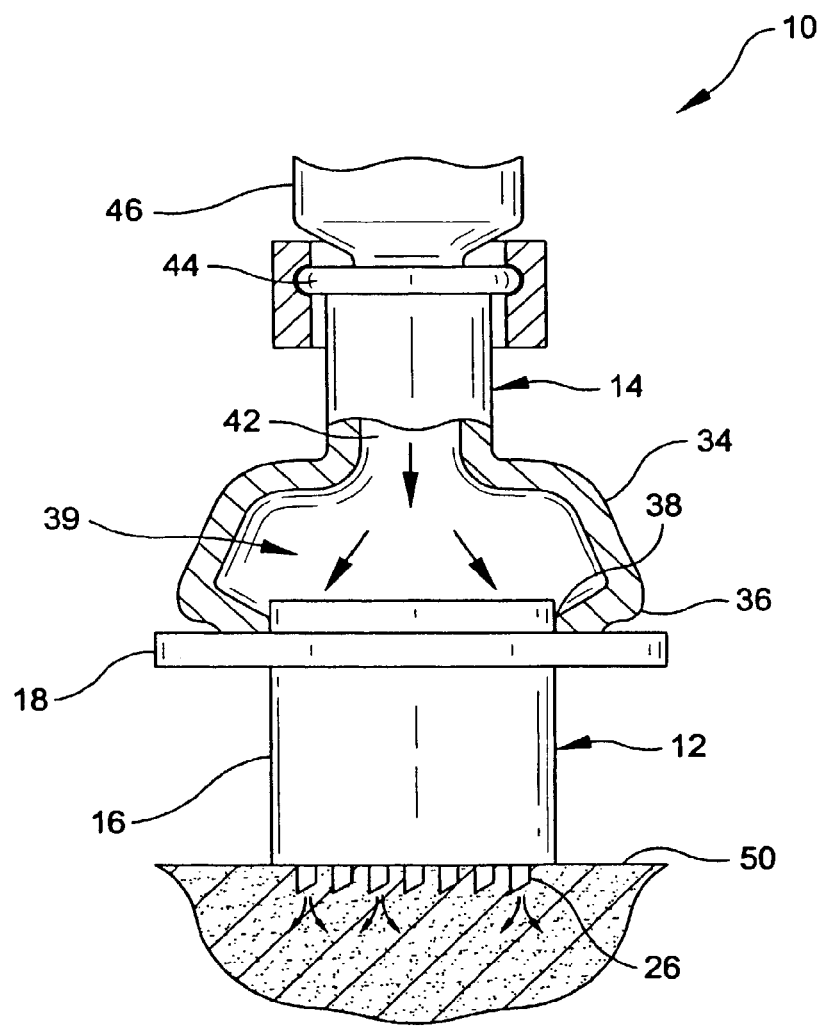
FIG. 5 is partial cross-sectional side elevational view of the transdermal delivery device of FIG. 1 showing the cavity for supplying the substance to the cannulas.

Coupling member 14 is attached to top end 20 of support 12 as shown in FIG. 5. In one embodiment, coupling member 14 can be attached to support 12 by a friction fit or by a suitable adhesive to form a fluid-tight seal between support 12 and coupling member 14. A fluid supply device 46 as shown in FIG. 1 is coupled to collar 44 to supply a substance to cannulas 26. In the embodiment illustrated, fluid supply member 46 is a standard syringe having a Luer fitting 48 for coupling with collar 44. In use, device 10 is pressed against the skin 50 of a patient with sufficient pressure for tip 32 of cannulas 26 to penetrate skin 50 to a desired depth. Fluid supply member 46 delivers a substance through coupling member 14 and through cannulas 26 where the substance is delivered into the skin of a patient.

In the embodiment of FIGS. 1-5, coupling member 14 is a separate member that is attached to support 12. In further embodiments, coupling member 14 can be integrally formed with support member. In still further embodiments, delivery device 10 can also be integrally formed with a fluid supply member. Fluid supply member 46 can be any suitable device capable of supplying a substance through device 10 to the tips 32 of cannulas 26 for delivering the substance into the skin of a patient. Fluid supply member 46 can be any suitable active delivery device such as a pump or passive delivery device for sustained delivery of a substance to the patient. Alternatively, a fluid absorbing device is coupled to support 12 to store fluids withdrawn from the patient.

Support 12 and cannulas 26 can be assembled using various methods. In the embodiment of FIGS. 1-5, a plurality of channels 24 extend axially through support 12 and are dimensioned to receive cannulas 26. Channels 24 are dimensioned to enable cannulas to be placed in channels by manual assembly or machine operations. A suitable adhesive is preferably applied to the outer surface of cannulas 26 prior to insertion into channels 24 to bond cannulas 26 in place and to form a fluid-tight seal between the outer wall of cannulas 26 and the wall of channels 24. In alternative embodiments, the cannulas can be positioned in the channels and an adhesive applied around the base of the cannula to bond the cannulas to the support. A fluid-tight seal around cannulas 26 adjacent bottom wall 22 is particularly desirable to ensure that the substance being delivered to the patient passes through the cannula where it can be delivered into the skin of the patient and not around the cannula. In a similar manner, providing a fluid-tight seal between the outer surface of cannulas and the surfaces of the channels prevents backflow of fluids upwardly between the wall of channels 24 and cannulas during active delivery of a substance through the cannulas. In further embodiments, the cannulas can be friction or press fitted into the channels. A suitable sealant or adhesive can be applied to seal the cannulas to the body as needed. Alternatively, the skin penetrating members can be bonded and sealed to the support by sonic or thermal welding.

Figure 6:
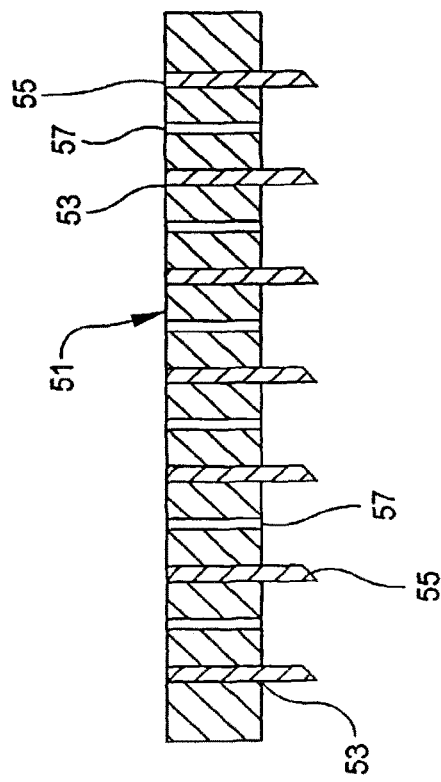
FIG. 6 is a cross-sectional side view of a support for a sampling or delivery device having solid penetrating members and fluid passages to the penetrating members.

FIG. 6 shows a further embodiment of a support 51 for a sampling or delivery device. In this embodiment, support 51 includes a plurality of axial channels 53 supporting a plurality of solid needles 55. Adjacent each needle 55 is a fluid passage 57 for supplying a substance to the patient or withdrawing a substance from the patient in the area of the needles 55.

Figure 7:
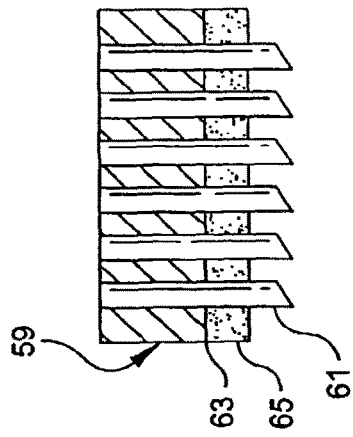
FIG. 7 is a cross-sectional side view of a support for a sampling device having solid needles and fluid absorbing substrate.
Figure 7A:
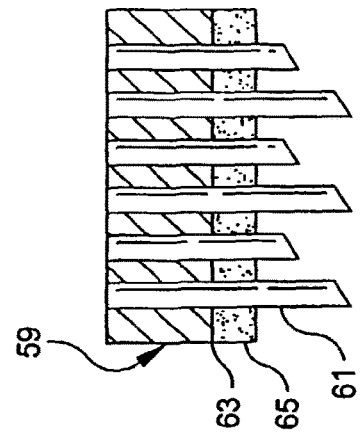

In a further embodiment shown in FIG. 7, a support 59 includes a plurality of needles 61 extending from a bottom end 63. A fluid absorbing material 65 is positioned on the bottom end of the support 59 for absorbing fluid withdrawn from the patient. Suitable absorbing materials can include an ion-conducting hydrogel as known in the art.

Figure 8:
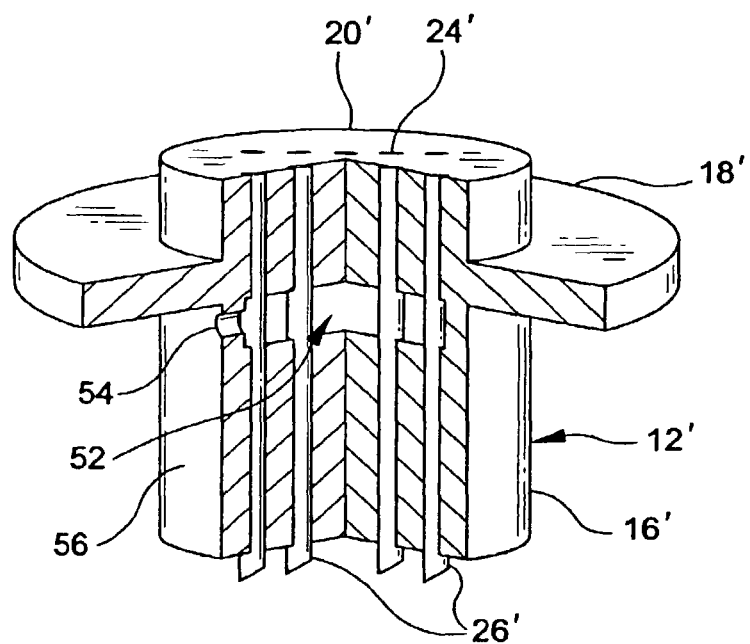
FIG. 8 is a perspective view in cross-section of the support for the cannulas in a second embodiment of the invention showing the cavity for introducing a sealant to seal the cannulas to the support.

FIG. 8 shows a further embodiment of the invention including a support 12' and a plurality of cannulas 26' coupled to support 12'. In this embodiment, support 12 is substantially the same as the support of the embodiment of FIGS. 1-5 except for recess 52, so that identical elements are identified by the same reference number with the addition of a prime.

Cylindrical body 16' includes a plurality of spaced-apart channels 24' extending axially through body 16' from top end 20' to bottom end 22'. A hollow cavity 52 is formed in cylindrical body 16' having an entry port 54 extending through a side wall 56 of body 16'. Cannulas 26' are placed in channels 24' with beveled tips 32' extending from bottom end 22'. After cannulas 26' are positioned in a desired location, an adhesive (not shown) is introduced through port 54 to fill cavity 52. The adhesive fills cavity 52 to secure cannulas 26' in place and seal channels 24' around cannulas 26'.

In the embodiment of FIG. 8, a single cavity 52 is provided to secure cannulas 26' in channels 24'. In further embodiments, additional cavities can be provided along the axial length of body 16'. In still further embodiments, two or more cavities can be provided to intersect only selected channels.

Figure 10:
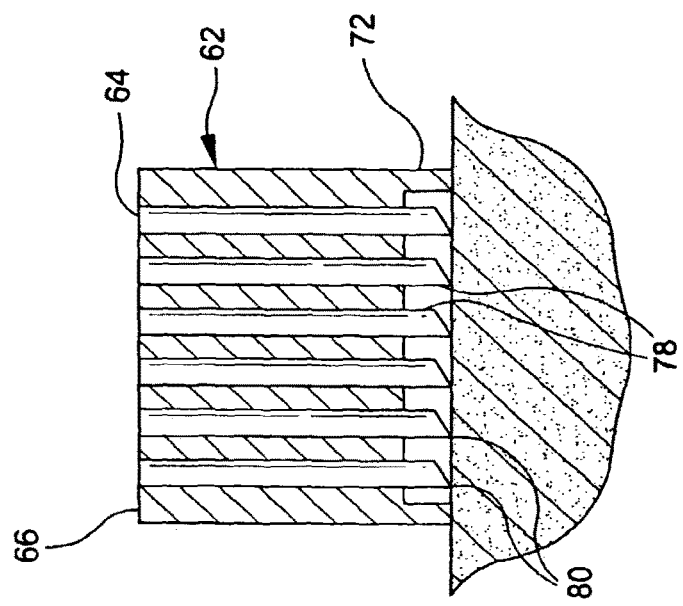
FIG. 10 is a cross-sectional view of the support of FIG. 7 showing the cannulas positioned in the support.
Figure 9:
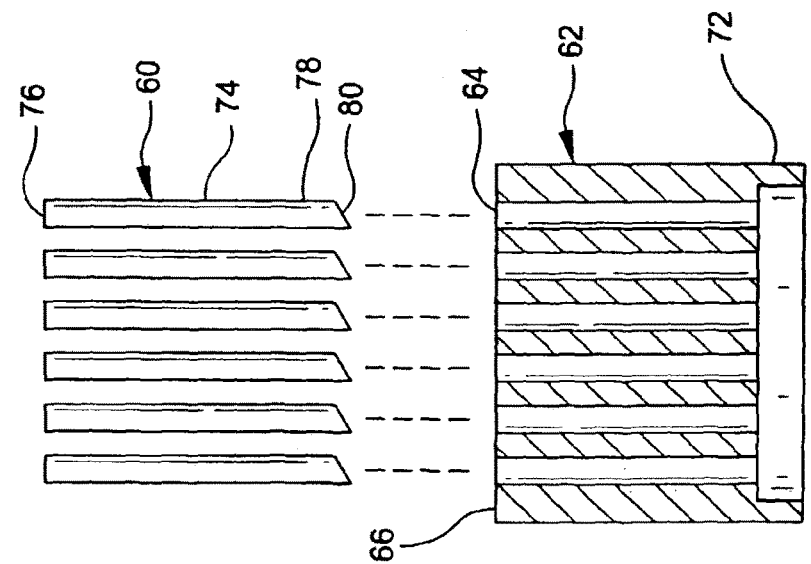
FIG. 9 is a side view in cross-section of the support for the cannulas during assembly of the delivery device in a further embodiment of the invention.
Figure 11:
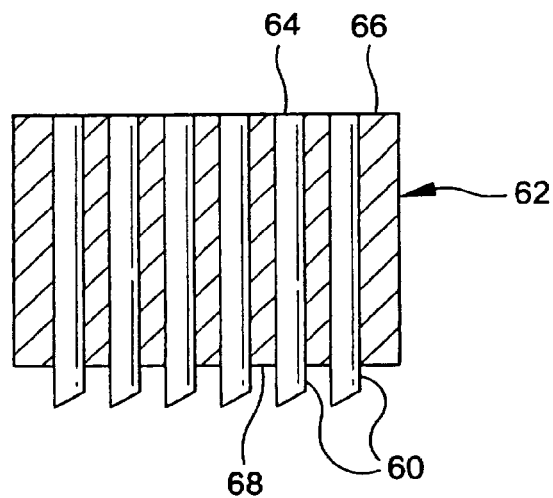
FIG. 11 is cross-sectional view of the support and cannulas of FIG. 8 showing the annular collar removed.

Referring to FIGS. 9-11, a further embodiment of a sampling or delivery device includes a plurality of skin penetrating members in the form of needles 60 mounted in a support 62. Support 62 is a solid body having a plurality of spaced-apart channels extending axially through support 62 from a top end to a bottom end. As shown in FIG. 9, support 62 includes a top face 66 and a bottom face 68. Bottom face 68 includes a recessed area 70 surrounded by a base in the form of an annular collar 72 extending axially from support 62. As shown, collar 72 is formed around the outer edge of bottom face 58 and encircles channels 64. Recessed area 70 has a depth corresponding substantially to the desired length of the exposed portion of needles 60.

Needles 60 have a generally cylindrical shape with a hollow body 74, a top end 76 and a bottom end 78. Bottom end 78 includes a beveled tip 80 as in the previous embodiment.

Referring to FIG. 10, the delivery device is assembled by placing a support 62 on a flat surface 82 with annular collar 72 contacting support 62. Needles 60 are then positioned in channels 64 with beveled tip 80 extending from bottom face 68 and resting on flat surface 62. In this manner, beveled tip 80 of each needle 60 is positioned in the same plane and have an effective length extending from bottom face 68 being substantially the same. As shown in FIG. 9, the height of annular collar 72 determines the effective length of needles 60 extending from bottom face 68. Needles 60 are then bonded to support 62 by a suitable adhesive or other bonding method as in the previous embodiments. Collar 72 is then removed by machining, stereo lithography or other methods to form a substantially flat bottom face 68 on support 62 with beveled tips 80 of needles 60 extending from bottom face 68 a uniform distance. In the illustrated embodiment, the skin penetrating members have a beveled tip formed before inserting the member into the support. In alternative embodiments, the skin penetrating members can have a blunt tip that is machined to form a sharp tip after being mounted in the support. A suitable coupling member and fluid supply member is then attached to support 62 for delivering a substance to needles 60 as in the previous embodiments.

The skin penetrating members are generally positioned in a support with a top end of the skin penetrating member being substantially flush with the top end of the support. In embodiments of the invention, skin penetrating members can have a length extending beyond the top end of the support to assist in the assembling operation. In embodiments where the top end of the skin penetrating members extend above the top surface of the support during assembly, the exposed portion of the top end of the skin penetrating members can be removed by a suitable machining operation.

Figure 12:
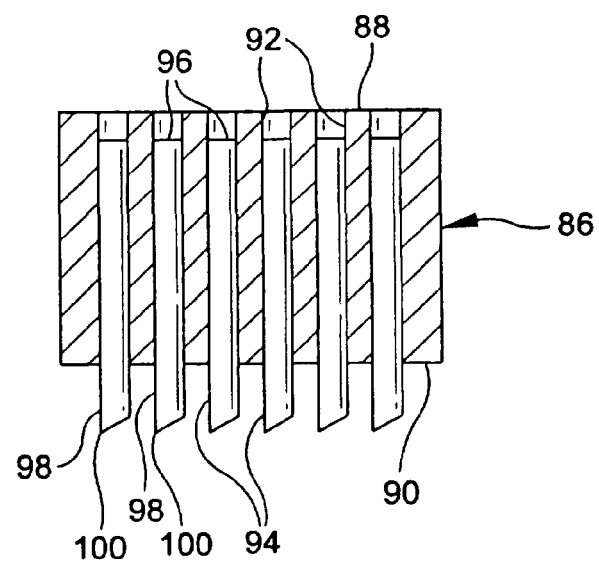
FIG. 12 is cross-sectional view of the support and cannulas in a further embodiment of the invention showing the cannulas having a top end spaced below the surface of the support.

In a further embodiment shown in FIG. 12, a support 86 includes a top end 88 and a bottom end 90. A plurality of channels 92 extend axially through support from top end 88 to bottom end 90. Cannulas 94 are positioned in channels 92. In this embodiment, cannulas 94 have a top end 96 recessed below top end in channels 92. Cannulas 94 also includes a bottom end 98 having a beveled tip 100 extending axially from bottom end 90 of support 86. In this embodiment, channels 92 form a fluid path for supplying a substance from a supply container to cannulas 94. As in the previous embodiments, an adhesive or sealant is provided between the outer surface of cannulas 94 and channels 92.

Figure 13:
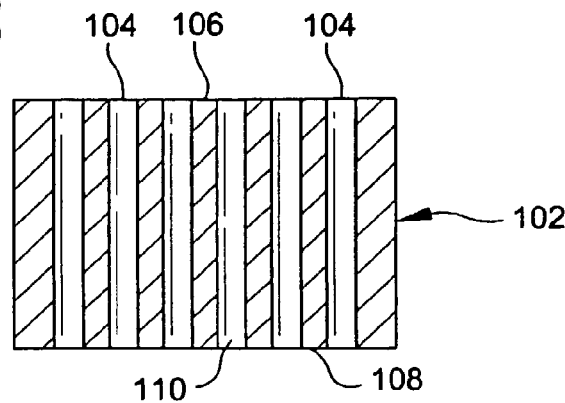
FIG. 13 is a cross-sectional view of the array of cannulas embedded in the support.
Figure 14:
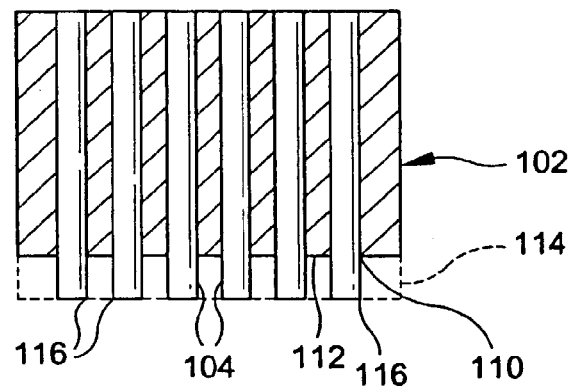
FIG. 14 is a cross-sectional view of the support partially etched to expose a portion of the cannulas.
Figure 15:
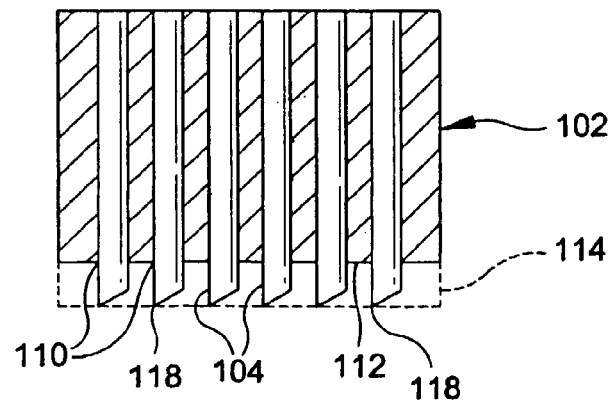
FIG. 15 is cross-sectional view of the support showing the cannulas cut at an angle to form a sharp tip on the cannulas.

Referring to FIGS. 13-15, a further embodiment for assembling the support 102 and cannulas 104 is shown. Support 102 includes a body portion having a top end 106 and a bottom end 108. A plurality of channels 110 extend axially through support 102 from top end 106 to bottom end 108. Cannulas 112 are positioned in channels 110 as shown in FIG. 13. In the embodiment shown, support 102 is formed with channels 110 during manufacture and cannulas 112 are inserted into channels 110. In a further embodiment, the skin penetrating members can be arranged into an array and the support 102 then can be molded from a plastic material around the skin penetrating members to form an integral unit.

Bottom portion 114 of support 102 as shown in FIG. 14 is removed by suitable methods to expose a desired effective length of cannulas 104. The support material can be removed by machining or etching methods as known in the art to expose cannulas 104. Preferably, the method for removing the support material forms a substantially flat bottom face 112. Cannulas 104 include a bottom end 116 that is machined to form a beveled tip 118. The resulting device is then attached to a suitable coupling member and fluid supply member as in the previous embodiments.

Figure 16:
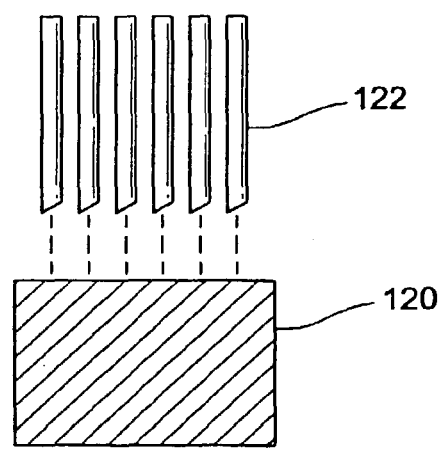
FIGS. 16-18 show a sequential side view of a further embodiment of an assembly of the device.
Figure 17:
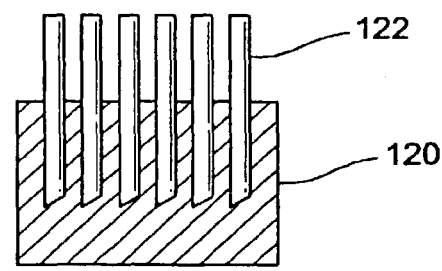
Figure 18:
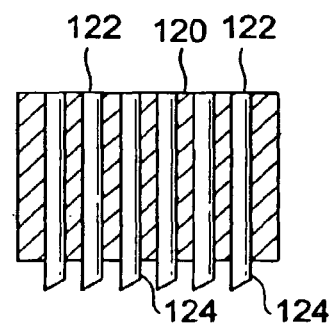

Referring to FIGS. 16-18, a further embodiment of the invention is shown for assembling the device. In this embodiment, a solid support 120 is provided and a plurality of skin penetrating members 122 are pushed through support 120. Support 120 is a plate made of a suitable material having sufficient strength to support skin penetrating member 122 and that can be pierced by skin penetrating members. As shown in FIGS. 16 and 17, skin penetrating members 122 are pushed to penetrate support 120. Skin penetrating members 122 are forced through support 120 to pierce support 120 to expose an end 124 of skin penetrating member 122 as shown in FIG. 18.

In the various illustrated embodiments of the invention, the cannulas are formed in a substantially uniform array covering a substantial portion of the bottom face of the support. The actual number of cannulas in the device can range generally from 1 to about 100 depending on the particular needs of the delivery device. The pattern of the array can also vary depending on the substance being delivered and the intended delivery site. The array can be formed in various rows and columns that are spaced apart to form areas without cannulas for penetrating the skin.

While various embodiments have been chosen to illustrate the invention, it will be appreciated by those skilled in the art that various modifications and additions can be made without departing from the scope of the invention as defined in the appended claims.

The invention claimed is:

1. A method of forming a device for penetrating the skin of a patient comprising the steps of:
   providing a support having a top end and a bottom end; and
   providing a plurality of skin penetrating members having a first end and a second end and coupling said first end of skin penetrating members to said support with said second end being spaced from said bottom end of said support,
   wherein said support includes a plurality of spaced apart channels, said method comprising positioning said skin penetrating members in said channels.

2. The method of claim 1, wherein said channels extend between said top end and said bottom end and said method comprises positioning said skin penetrating members in said channels in said support where said first end of said skin penetrating member is substantially flush with said top end.

3. The method of claim 2, comprising positioning said skin penetrating members in said channels in said support where said first end is spaced from said top end and is recessed in said channels.

4. The method of claim 1, comprising positioning said skin penetrating members in said channels where said second end is spaced from said bottom end a distance of about 10 microns to about 500 microns.

5. The method of claim 1, comprising bonding said skin penetrating members to said support with an adhesive.

6. The method of claim 1, comprising bonding said skin penetrating members by thermal welding or sonic welding.

7. The method of claim 1, wherein said skin penetrating members are coupled to said support by a friction fit.

8. The method of claim 1, wherein said support has a base extending axially from said bottom end, said method comprising placing said base against a planar member, positioning said skin penetrating members in said channels whereby said second ends of said skin penetrating members contact said planar member, coupling said skin penetrating members to said support, and separating said base from said support.

9. The method of claim 8, wherein said base is an annular collar.

10. The method of claim 1, comprising the step of arranging said skin penetrating members in an array and molding said support around said array to couple said skin penetrating members to said support.

* * * * *